US012612625B2

(12) United States Patent
Baram et al.

(10) Patent No.: US 12,612,625 B2
(45) Date of Patent: *Apr. 28, 2026

(54) COMPOSITIONS FOR GENOME EDITING

(71) Applicant: EmendoBio Inc., Wilmington, DE (US)

(72) Inventors: David Baram, Tel Aviv (IL); Lior Izhar, Tel Aviv (IL); Rafi Emmanuel, Ramla (IL)

(73) Assignee: EmendoBio Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/477,291

(22) Filed: Sep. 28, 2023

(65) Prior Publication Data

US 2024/0132884 A1 Apr. 25, 2024
US 2024/0229024 A9 Jul. 11, 2024

Related U.S. Application Data

(63) Continuation of application No. 16/341,820, filed as application No. PCT/US2017/059077 on Oct. 30, 2017, now Pat. No. 11,795,453.

(60) Provisional application No. 62/436,963, filed on Dec. 20, 2016, provisional application No. 62/415,116, filed on Oct. 31, 2016.

(51) Int. Cl.
| | |
|---|---|
| *C12N 15/11* | (2006.01) |
| *C12N 9/22* | (2006.01) |
| *C12N 15/90* | (2006.01) |

(52) U.S. Cl.
CPC .............. *C12N 15/111* (2013.01); *C12N 9/22* (2013.01); *C12N 15/11* (2013.01); *C12N 15/902* (2013.01); *C12N 2310/20* (2017.05)

(58) Field of Classification Search
None
See application file for complete search history.

(56) References Cited

U.S. PATENT DOCUMENTS

| | | | | |
|---|---|---|---|---|
| 2004/0048378 A1* | 3/2004 | Rozwadowski | ..... | C07K 14/245 |
| | | | | 514/44 A |
| 2013/0284599 A1 | 10/2013 | Ye et al. | | |
| 2016/0168593 A1 | 6/2016 | Cost et al. | | |
| 2016/0208272 A1 | 7/2016 | Cigan et al. | | |
| 2016/0304871 A1* | 10/2016 | Rigo | ...................... | A61P 21/00 |
| 2021/0371857 A1 | 12/2021 | Baram et al. | | |

OTHER PUBLICATIONS

Convertini et al., Role of FOXA and Sp1 in mitochondrial acylcarnitine carrier gene expression in different cell lines. Biochemical and Biophysical Research Communication (2011) 404(1):376-381 (Year: 2011).*

Song et al., Improved hematopoietic differentiation efficiency of gene-corrected beta-thalassemia induced pluripotent stem cells by CRISPR/Cas9 system. Stem Cells and Development (2015), 24: 1053-1065 (Year: 2015).*

Chu et al., Increasing the efficiency of homology-directed repair for CRISPR-Cas9-induced precise gene editing in mammalian cells. Nature Biotechnology (2015) 33:5, 543-548) (Year: 2015).*

Sellak et al., Sp1 transcription factor as a molecular target for nitric oxide- and cyclic nucleotide-mediated suppression of cGMP-dependent protein kinase-1alpha expression in vascular smooth muscle cells. Circulation Research (2002), 90(4):405-412 (Year: 2002).*

Croze et al., ROCK Inhibition Extends Passage of Pluripotent Stem Cell-Derived Retinal Pigmented Epithelium. Stem Cells Translational Medicine (2014), 3(9):1066-78 (Year: 2014).*

Chin et al., Triplex-forming peptide nucleic acids induce heritable elevations in gamma-globin expression in hematopoietic progenitor cells. Molecular Therapy (2013), 21(3):580-587 (Year: 2013).*

StemSpan™ CC100. StemCell Technologies https://www.stemcell.com/products/stemspan-cc100.html. Retrieved from internet, [Retrieved Mar. 2, 2022] (Year: 2022).*

Cong et al., Multiplex genome engineering using CRISPR/Cas systems. Science (2013) 339:819-823 (Year: 2013).*

Renaud et al., Improved genome editing efficiency and flexibility using modified oligonucleotides with TALEN and CRISPR-Cas9 nucleases. Cell Reports (2016), 14: 2263-2272 (Year: 2016).*

Ahn et al., TATA binding proteins can recognize nontraditional DNA sequences. Biophysical Journal (2012), 103: 1510-1517 (Year: 2012).*

Worrad et al., Regulation of gene expression in the preimplantation mouse embryo: temporal and spatial patterns of expression of the transcription factor Sp1. Molecular Reproduction and Development (1997), 46:268-277 (Year: 1997).*

Grundström et al., The transcription factor E2A can bind to and cleave single-stranded immunoglobulin heavy chain locus DNA. Molecular Immunology (2023), 153: 51-59 (Year: 2023).*

Lam and Dean. Progress and prospects: nuclear import of nonviral vectors. Gene Therapy (2010) 17, 439-447 (Year: 2010).*

Chrenek et al., CRISPR challenges in treating retinal disease. Asia Pac J Ophthalmol (Phila) (2016), 5(4): 304-308 (Year: 2016).*

Curran, E. (2017). Discovery of novel TAF1 DNA binding domains in TFIID promoter recognition and gene transcription (Doctoral dissertation). (Year: 2017).*

Pan et al., E-box binding transcription factors in cancer. Front. Oncol. (2023), 13:1223208 (Year: 2023).*

Ji et al., "Multiple and Essential Sp1 Binding Sites in the Promoter for Transforming Growth Factor-b Type I Receptor", J Biol Chem., 1997, vol. 272(34), p. 21260-7.

(Continued)

*Primary Examiner* — Catherine Konopka

(74) *Attorney, Agent, or Firm* — Faegre Drinker Biddle & Reath LLP

(57) ABSTRACT

The present invention relates to compositions and methods for increasing the rate of site specific insertion of a donor DNA sequence to the genome. More specifically, the method introduces a donor DNA template containing at least one transcription factor binding site to a cell in order to favor specific insertion of a donor template sequence at a target site by homology directed repair (HDR).

11 Claims, 3 Drawing Sheets

(56)        References Cited

OTHER PUBLICATIONS

Tian et al., "Allelic Mutations in Noncoding Genomic Sequences Construct Novel Transcription Factor Binding Sites that Promote Gene Overexpression," Genes Chromosomes Cancer, 2015, vol. 54(11), p. 692-701.

Written Opinion of the International Searching Authority issued Mar. 26, 2018 in connection with PCT International Application No. PCT/US2017/059077.

International Search Report issued Mar. 26, 2018 in connection with PCT International Application No. PCT/US2017/059077.

Knauert and Glazer. Triplex forming oligonucleotides: sequence-specific tools for gene targeting: Human Molecular Genetic (2001), 10: 2243-2251.

Lam and Dean, Progress and prospects: nuclear import of nonviral vectors. Gene Therapy (2010) 17, 439-447.

Chrenek et al., CRISPR challenges in treating retinal disease. Asia Pac J. Ophthalmol (Phila) (2016), 5(4): 304-308.

Park et al., Antifibrotic effect through the regulation of transcription factor using ring type-Spl decoy oligodeoxynucleotide in carbon tetrachloride-induced liver fibrosis. The Journal of Gene Medicine (2009), 11: 824-833.

Gee et al., Triplex formation prevents Spl binding to the dihydrofolate reductase promoter. Journal of Biological Chemistry (1992), 267(16); 11163-11167.

Chan et al., Targeted Correction of an Episomal Gene in Mammalian Cells by a Short DNA Fragment Tethered to a Triplex-forming Oligonucleotide. Journal of Biological Chemistry (1999), 274(17); 11541-11548.

Convertini et al., Role of FOXA and Spl in mitochondrial acylcarnitine carrier gene expression in different cell lines. Biochemical and biophysical Research communication (2011) 404(1); 376-381.

Song et al., Improved hematopoietic differentiation efficiency of gene-corrected beta-thalassemia induced pluripotent stem cells by CRISPR/Cas9 system. Stem Cells and Development (2015) 33:5, 543-548.

Chu et al., Increasing the efficiency of homology-directed repair for CRISPR-Cas9-induced precise gene editing in mammalian cells. Nature Biotechnology (2015) 33:5, 543-548.

Sellak et al., Spl transcription factor as a molecular target for nitric oxide-and cylic nucleotide-mediated suppression of CGMP-dependent protein kinase-lapha expression in vascular smooth muscle cells. Circulation Research (2002) 90(4): 405-412.

Croze et al., ROCK inhibition Extends Passage of Pluripotent Stem-Cell-Derived Retinal Pigmented Epithelium. Stem Cells Translational Medicine (2014), 3(9): 1066-78.

Chin et al., Triplex-forming peptide nucleic acids induce heritable elevations in gamma-goblin expression in hematopoietic progenitor cells. Molecular Therapy (2013), 21(3): 580-587.

Cong et al., Multiplex genome engineering using CRISPR/Cas systems. Science (2013) 339: 819-823.

* cited by examiner

COMPOSITIONS FOR GENOME EDITING

CROSS-REFERENCE TO RELATED APPLICATIONS

This application is a continuation of U.S. application Ser. No. 16/341,820, filed Apr. 12, 2019, which is a § 371 national stage of PCT International Application No. PCT/US2017/059077, filed Oct. 30, 2017, claiming the benefit of U.S. Provisional Application Nos. 62/436,963, filed Dec. 20, 2016, and 62/415,116, filed Oct. 31, 2016, the entire contents of each of which are hereby incorporated by reference in their entirety.

Throughout this application, various publications are referenced, including referenced in parenthesis. Full citations for publications referenced in parenthesis may be found listed at the end of the specification immediately preceding the claims. The disclosures of all referenced publications in their entireties are hereby incorporated by reference into this v application in order to more fully describe the state of the art to which this invention pertains.

The present invention relates to compositions and methods for increasing the rate of site specific insertion of a donor DNA sequence to a genomic DNA target site. More specifically, the method comprises introducing a donor DNA template which contains at least one transcription factor binding site to a cell in order to favor specific insertion of a donor template sequence at a target site by homology directed repair (HDR).

BACKGROUND

Targeted genome modification is a powerful tool that can be used to reverse the effect of pathogenic genetic variations and therefore has the potential to provide new therapies for human genetic diseases. Current genome engineering tools, including engineered zinc finger nucleases (ZFNs), transcription activator-like effector nucleases (TALENs), and most recently, RNA-guided DNA endonucleases such as CRISPR/Cas, produce sequence-specific DNA breaks in a genome. The modification of the genomic sequence occurs at the next step and is the product of the activity of one of two cellular DNA repair mechanisms triggered in response to the newly formed DNA break. These mechanisms include: (1) non-homologous end-joining (NHEJ) in which the two ends of the break are ligated together in a fast but also inaccurate manner (i.e. frequently resulting in mutation of the DNA at the cleavage site in the form of small insertion or deletions) and (2) homology-directed repair (HDR) in which an intact homologous DNA donor is used to replace the DNA surrounding the cleavage site in an accurate manner. In addition. HDR can also mediate the precise insertion of external DNA at the break site.

A major drawback of current genome engineering tools is the lack of ability to control the division of labor between the cellular DNA repair mechanisms. As a result, the DNA breaks that are generated using these tools are repaired stochastically by either NHEJ or HDR. This stochastic nature of repair frequently leads to a futile outcome that significantly reduces the efficiency and accuracy of the process. For example, reversing the pathogenic effect of disease-causing genetic variations requires, in many cases, the insertion of a DNA element from an external source at the break site. This activity is exclusively mediated by HDR. However, using the currently available genome editing tools, the majority of breaks will be subjected to repair via NHEJ which is the dominant process. In such cases, NHEJ not only outcompetes HDR on repairing the initial DNA breaks, but it is also likely to result in mutation of the original sequence.

SUMMARY OF THE INVENTION

The present invention provides compositions and methods for increasing the efficiency of HDR for genome editing applications. The composition comprises a donor DNA template bound by a transcription factor which is delivered to cells in order to promote elevated HDR repair rates of DNA breaks. The process results in the desired insertion of the DNA donor sequence at the correct genomic locus in a higher proportion of cells. The elevated rate of insertion of the DNA donor sequence at the target site when using the compositions and methods of the subject invention is measured relative to repair of a DNA break in a cell that receives DNA donor alone. i.e. a donor which is not bound by the transcription factor.

The present invention provides a composition comprising a donor DNA template which contains at least one transcription factor binding site. The donor DNA template generally contains regions of homology flanking a desired insertion or recombination sequence. The regions of homology share sequence similarity with a target gene. A transcription factor bound to the donor DNA template enhances import of the donor DNA template to the nucleus.

In some embodiments, wherein the transcription factor triggers transcription of a target gene.

In some embodiments, wherein the transcription factor enhances transcription of a target gene.

In some embodiments, wherein the donor DNA template is single-stranded DNA.

In some embodiments, wherein a transcription factor binding site on the donor DNA template is located at a hairpin loop at a terminus of the donor DNA template.

In some embodiments, wherein the composition further comprises a second complimentary DNA strand, wherein the second complimentary DNA strand hybridizes with the single-stranded donor DNA template to form a donor DNA template assembly, and wherein the at least one transcription factor binding site is located at a hybridized portion of the donor DNA template assembly.

In some embodiments, the donor DNA template is double-stranded DNA.

In some embodiments, wherein the transcription factor binding site is a binding site for a transcription factor selected from the group consisting of Sp1, TBP, TAFs, E2F. E-box and YY1.

In some embodiments, the composition of the subject invention further comprises an RNA-guided DNA nuclease, or a polynucleotide encoding an RNA-guided DNA nuclease. However, any specific nuclease can be used to induce a DSB at a desired genomic target site including, but not limited to, zinc-finger nucleases, transcription activator-like effector nucleases, meganucleases, or other nucleases known in the art.

In some embodiments, the composition of the subject invention further comprises a guide-RNA, or a polynucleotide encoding a guide-RNA. The guide-RNA targets the RNA-guided DNA nuclease to an intended target site in the genome of the cell.

In some embodiments, wherein the composition of the subject invention further comprises an inhibitor of non-homologous end joining (NHEJ). Any elements that reduce or inhibit the incidence of NHFJ are considered inhibitors of NHFJ, including but not limited to siRNAs, antisense mRNA, and dominant negative forms which reduce or inhibit the presence or activity of NHEJ factors in a cell. Such NHEJ inhibitors are particularly useful in biasing the cellular DNA-repair pathway toward HDR during the G1 phase of the cell cycle.

In some embodiments, wherein the composition further comprises a proliferation factor. The proliferation factor may be LIN28 and/or VEGF-A. Preferably, the proliferation factor induces on average less than five cellular divisions.

The present invention also provides a method for editing a genome in a cell comprising delivering to the cell a donor DNA template which contains at least one transcription factor binding site.

In some embodiments, wherein the transcription factor triggers transcription of a gene being targeted for genome editing.

In some embodiments, wherein the transcription factor enhances transcription of a gene being targeted for genome editing In some embodiments, wherein the donor DNA template is single-stranded DNA.

In some embodiments, wherein a transcription factor binding site on the donor DNA template is located at a hairpin loop at a terminus of the donor DNA template.

In some embodiments, wherein the method further comprises delivering a second complimentary DNA strand, wherein the second complimentary DNA strand hybridizes with the single-stranded donor DNA template to form a donor DNA template assembly, and wherein the at least one transcription factor binding site is located at a hybridized portion of the donor DNA template assembly.

In some embodiments, the donor DNA template is double-stranded DNA.

In some embodiments, wherein the transcription factor binding site is a binding site for a transcription factor selected from the group consisting of Sp1, TBP, TAFs, E2F, E-box and YY1.

In some embodiments, further comprising delivering to the cell an RNA-guided DNA nuclease, or a polynucleotide encoding an RNA-guided DNA nuclease.

In some embodiments, further comprising delivering to the cell a guide-RNA, or a polynucleotide encoding a guide-RNA.

In some embodiments, further comprising delivering to the cell an inhibitor of non-homologous end joining.

In some embodiments, further comprising delivering to the cell a proliferation factor.

The present invention provides a host cell having a genomic edit created by any one of the methods described herein.

The present invention provides any one of the compositions described herein used in the manufacture of a medicament.

The present invention provides a pharmaceutical composition comprising any one of the compositions described herein.

The present invention provides a method of treating a genetic disease in a patient comprising administering to the patient the pharmaceutical composition as described above.

The present invention provides a use of a composition comprising a donor DNA template which contains at least one transcription factor binding site for triggering transcription of a target gene.

The present invention provides the use of any composition recited herein comprising a donor DNA template which contains at least one transcription factor binding site for triggering transcription of a target gene.

The present invention provides a composition comprising a donor DNA template which contains at least one transcription factor binding site for use in triggering transcription of a target gene.

The present invention provides any composition recited herein comprising a donor DNA template which contains at least one transcription factor binding site for use in triggering transcription of a target gene.

The present invention provides a medicament comprising a donor DNA template which contains at least one transcription factor binding site for use in triggering transcription of a target gene.

The present invention provides any medicament recited herein comprising a donor DNA template which contains at least one transcription factor binding site for use in triggering transcription of a target gene.

The present invention provides a kit when used to trigger transcription of a target gene comprising:

a) a composition comprising a donor DNA template which contains at least one transcription factor binding site, and b) instructions for introducing the composition into the cells.

The present invention provides a kit when used to trigger transcription of a target gene comprising:

a) any composition recited herein comprising a donor DNA template which contains at least one transcription factor binding site, and b) instructions for introducing the composition into the cells.

The present invention provides a use of a donor DNA template which contains at least one transcription factor binding site for editing a genome in a cell comprising delivering to the cell the donor DNA template.

The present invention provides the use of any donor DNA template recited herein which contains at least one transcription factor binding site for editing a genome in a cell comprising delivering to the cell the donor DNA template.

The present invention provides a donor DNA template which contains at least one transcription factor binding site for use in editing a genome in a cell comprising delivering to the cell the donor DNA template.

The present invention provides any donor DNA template recited herein which contains at least one transcription factor binding site for use in editing a genome in a cell comprising delivering to the cell the donor DNA template.

The present invention provides a medicament comprising a donor DNA template which contains at least one transcription factor binding site for use in editing a genome in a cell, wherein the medicament is delivered to the cell.

The present invention provides any medicament recited herein comprising a donor DNA template which contains at least one transcription factor binding site for use in editing a genome in a cell, wherein the medicament is delivered to the cell.

The present invention provides a kit when used to edit a genome in a cell comprising:

a) a composition comprising a donor DNA template which contains at least one transcription factor binding site, and b) instructions for introducing the composition into the cells.

The present invention provides a kit when used to edit a genome in a cell comprising:

a) any composition recited herein comprising a donor DNA template which contains at least one transcription factor binding site, and b) instructions for introducing the composition into the cells.

Each embodiment disclosed herein is contemplated as being applicable to each of the other disclosed embodiments. Thus, all combinations of the various elements described herein are within the scope of the invention.

DETAILED DESCRIPTION OF THE INVENTION

Figure 1:
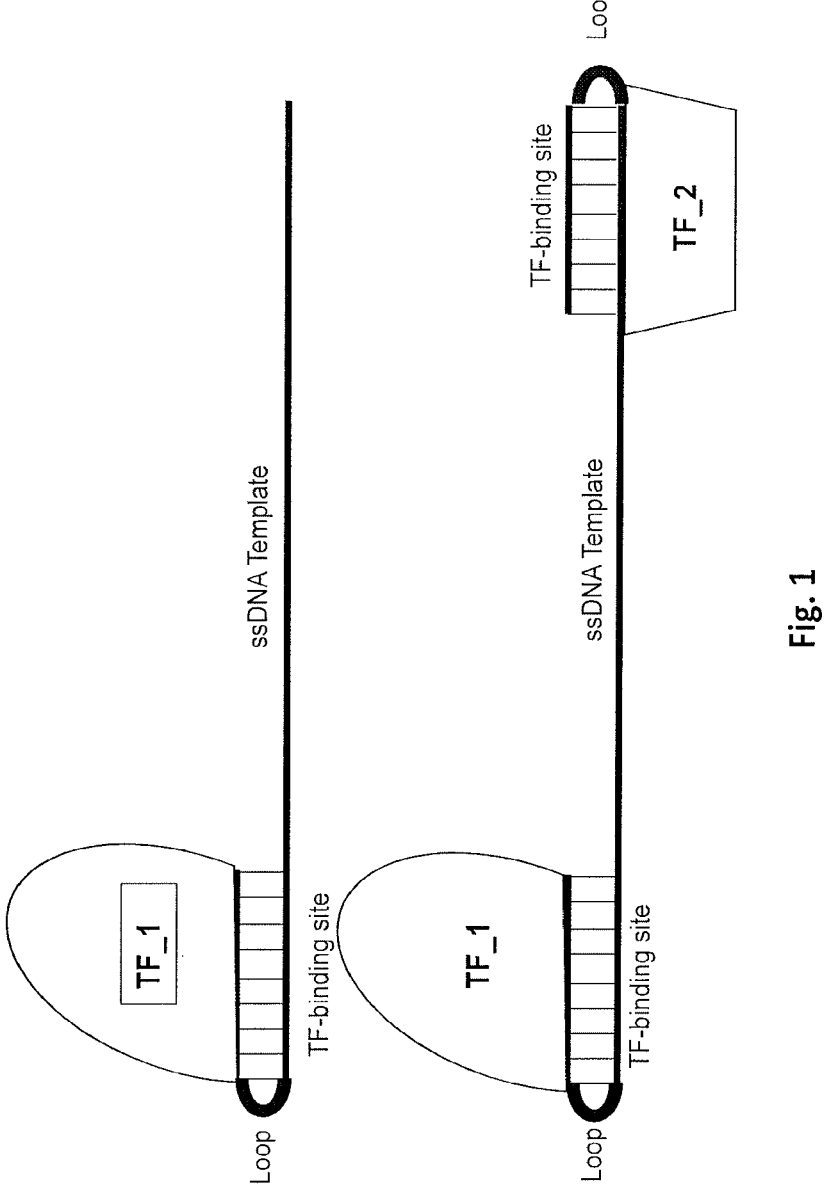
FIG. 1: A schematic of two embodiments of the present invention comprising a donor DNA template bound by at least one transcription factor at a transcription factor binding site. A ssDNA template contains a self-annealing sequence connected by a loop, thus forming a hairpin, at one (top panel) or both (bottom panel) termini. The hairpin contains a transcription factor binding site which binds a transcription factor. In the bottom panel, each hairpin contains a distinct transcription factor binding site and thus each hairpin binds a different transcription factor.
Figure 2A:
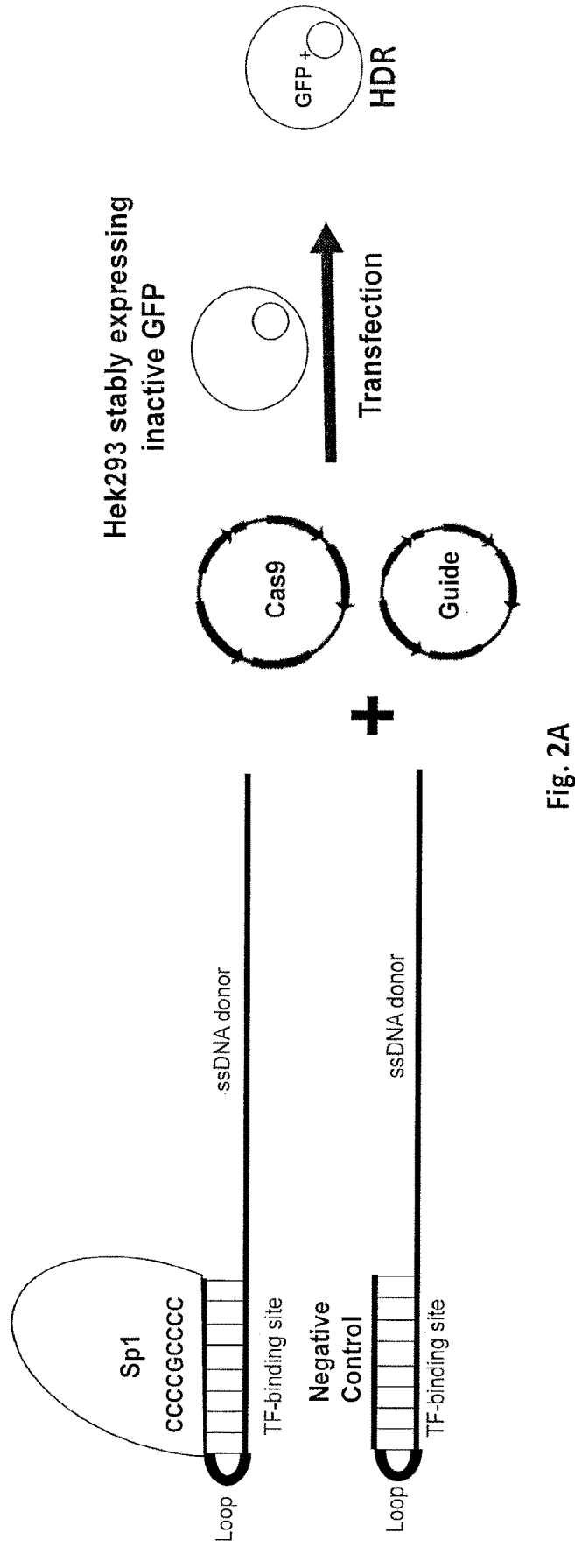
FIGS. 2A-2B: To measure the increase in HDR efficiency produced by inducing nuclear import of a DNA donor via a bound transcription factor, a Sp1 binding site was added to a DNA donor encoding active GFP and said DNA donor was transfected into HEK293 cells expressing inactive GFP. Various concentrations of ssDNA donor with or without a transcription factor binding site were transfected with constructs expressing a Cas9 nuclease and a guide RNA to direct the Cas9 nuclease to a target site. At 72 h post transfection the efficiency of HDR was measured by FACS (FIG. 2A). According to the results, the addition of the Sp1 binding site caused a two-fold induction in HDR rate relative to the donor without a transfection factor binding site (FIG. 2B).
Figure 2B:
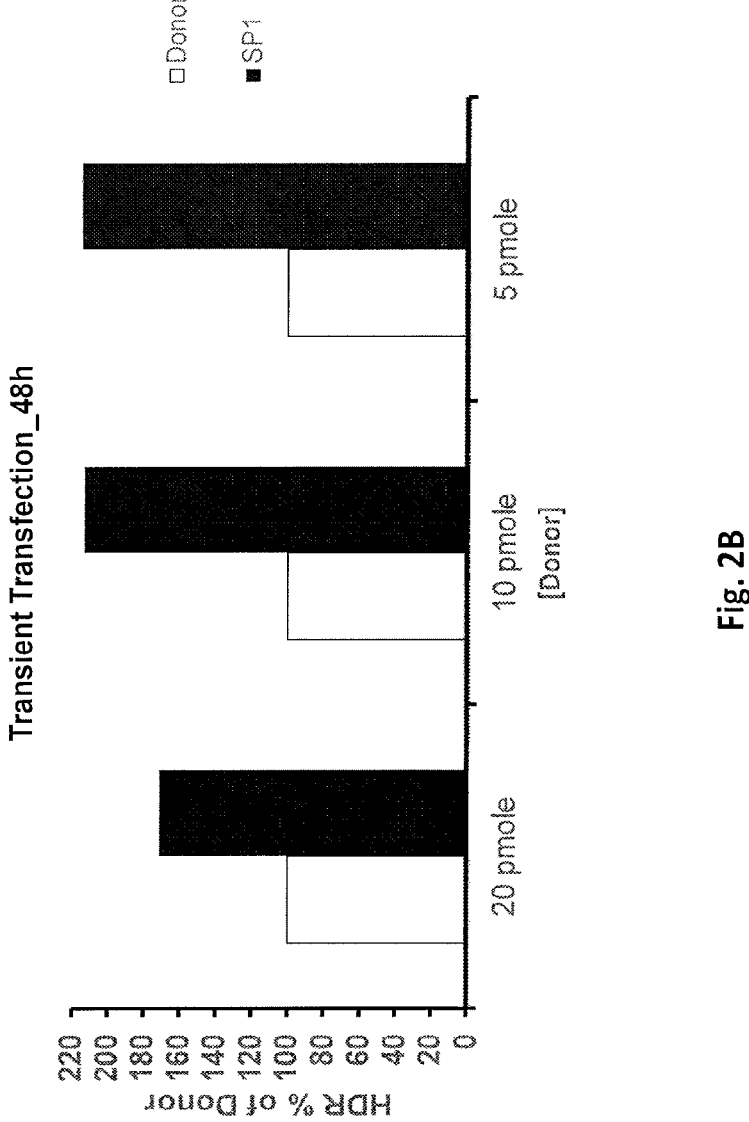

For inducing gene correction following double strand break, it is required to have a donor template in the vicinity of the double strand break. To achieve this purpose, the present invention discloses a composition comprising a donor DNA template containing a transcription factor (TF) binding site/s (e.g. binding site/s for Sp1, TBP, TAFs, E2F, E-box, YY1, etc.) at one or both termini. Once in the cytosol, transcription factors will bind to the TF binding site of the donor DNA template of the present invention, and mediate the active internalization of the donor DNA template into the nucleus. The binding of the TF to the TF binding site of the donor DNA template is considered reversible due to the short binding site (~20 bps) that does not enable the binding of additional factors that would stabilize the complex. Following the import into the nucleus the donor would be used as a template for HDR (either as a free template or still bound with the TF).

Thus, described herein are compositions and methods for increasing the efficiency of HDR-mediated repair by delivering to a cell a donor DNA template containing at least one transcription factor binding site.

Terms

Unless otherwise defined, all technical and scientific terms used herein have the same meaning as commonly understood by a person of ordinary skill in the art to which this invention belongs.

The terms "nucleic acid," "polynucleotide." and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acid.

"Targeted insertion" as used herein refers to the result of a successful genetic recombination event wherein a desired portion of a donor DNA sequence is inserted into a desired position in the genome of a cell. "Targeted insertion" also refers to the result of a successful genetic recombination event wherein a desired portion of a donor DNA sequence was copied into a desired position in the genome of a cell. "Genetic recombination" as used herein refers to any mechanism which introduces a sequence from one nucleic acid molecule to another molecule or to a different location on the same molecule. Thus, a "genetic recombination" mechanism may utilize insertion or copying, directly or indirectly e.g., via an intermediate.

The use of the donor DNA template which contains at least one transcription factor binding site of the present invention for genome editing results in an increase of the rate of targeted insertions. This increase can be calculated by quantifying the percentage of cells in a cell population where a targeted insertion event has occurred as a result of nuclease mediated genome editing. Various assays have been described that enable the determination of targeted insertion rates using the genome editing systems described herein. Assay systems for measuring targeted insertion of ZFN mediated genome editing have been described in U.S. Pat. No. 7,951,925. Assay systems for measuring targeted insertion of Cas9 mediated genome editing have been described in U.S. Provisional 61/823,689. Assay systems for measuring targeted insertion of TALEN mediated genome editing have been described in U.S. Pat. No. 8,586,526. Assay systems for measuring targeted insertion of meganuclease mediated genome editing have been described in U.S. Patent Publication No. 20070117128. These assay and other assays that are known in the art may be used to quantify the targeted insertion rate as mediated by the donor DNA template which contains least one transcription factor binding site of the present invention.

The term "off-target excision of the genome" as used herein refers to the percentage of cells in a cell population where the DNA of a cell was excised by a nuclease at an undesired locus during or as a result of genome editing. The detection and quantification of off-target insertion events can be done by known methods.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" or "TALEN" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. As a non-limiting example, See, e.g., U.S. Pat. No. 8,586,526.

"DNA breaks" refer to both single strand breaks (SSB) and double strand breaks (DSB). SSB are breaks that occur in one of the DNA strands of the double helix. DSB are breaks in which both DNA strands of the double helix are severed.

"DNA Cleavage" refers to the breakage of the covalent backbone of a DNA molecule. DNA cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events at two adjacent loci in the genome. DNA cleavage can result in the production of either blunt ends or staggered ends.

The term "nucleotide sequence" refers to a nucleotide sequence of any length, which can be DNA or RNA, can be linear, circular or branched and can be either single-stranded or double stranded. The term "donor sequence" refers to a nucleotide sequence that is inserted or copied into a genome. A donor sequence can be of any length, for example between 2 and 10,000 nucleotides in length (or any integer value there between or there above), preferably between about 100 and 1.000 nucleotides in length (or any integer there between), more preferably between about 200 and 500 nucleotides in length.

A "target site" or "target sequence" is a nucleic acid sequence that defines a portion of a nucleic acid to which a DNA binding protein or a fragment thereof can specifically bind, provided sufficient conditions for binding exist.

In this document, the terms "donor DNA template" and "DNA donor template" are used interchangeably. A donor DNA template can contain at least one transcription factor binding site, and can also contain a donor template which is fused to at least one transcription factor binding site.

A "donor DNA template assembly" is a DNA assembly comprising a single-stranded donor DNA template that is hybridized with a short complimentary DNA strand by annealing, preferably wherein a hybridized portion of the donor DNA template assembly contains a transcription factor binding site.

An "exogenous" molecule is a molecule that is not normally present in a cell, but can be introduced into a cell by one or more genetic, biochemical or other methods.

"Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

Expression of a protein in a cell can result from delivery of the protein to the cell or by delivery of a polynucleotide encoding the protein to a cell, wherein the polynucleotide is transcribed, and the transcript is translated, to generate the protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product, as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Plant" cells include, but are not limited to, cells of monocotyledonous (monocots) or dicotyledonous (dicots) plants. Non-limiting examples of monocots include cereal plants such as maize, rice, barley, oats, wheat, sorghum, rye, sugarcane, pineapple, onion, banana, and coconut. Non-limiting examples of dicots include tobacco, tomato, sunflower, cotton, sugarbeet, potato, lettuce, melon, soybean, canola (rapeseed), and alfalfa. Plant cells may be from any part of the plant.

"Eukaryotic" cells include, but are not limited to, fungal cells (such as yeast), plant cells, animal cells, mammalian cells and human cells. Cells may be isolated or not, or in culture or not.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

A "functional fragment" or a "functional derivative" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. The ability of a protein to interact with another protein can be determined, for example, by co-immunoprecipitation, two-hybrid assays or complementation, both genetic and biochemical. See, for example. Fields et al. (1989) Nature 340:245-246; U.S. Pat. No. 5,585,245 and PCT WO 98/44350.

The term "nuclease" as used herein refers to an enzyme capable of cleaving the phosphodiester bonds between the nucleotide subunits of nucleic acid. A nuclease may be isolated or derived from a natural source. A nuclease may be altered or modified to change its activity. For instance, alterations or modifications to a nuclease may change its activity from double-strand break formation to single-strand break formation. The natural source may be any living organism. Alternatively, a nuclease may be a modified or a synthetic protein which retains the phosphodiester bond cleaving activity.

DNA Repair by Homologous Recombination

The term "homology directed repair" (HDR) refers to a mechanism by which cells repair DNA damage (double strand DNA lesions and single strand nicks). One form of HDR is homologous recombination (HR).

Homologous recombination (HR) is mediated through the Rad52 family of proteins. Rad52 interacts and co-localizes with Rad51, induces Rad51 activity, binds preferentially to DSBs and protects them from exonuclease activity. The initial cellular response to DSBs is mediated through ATM (Ataxia Telangiectasia Mutated) and MRN Complex (Mre11-Rad50-NBS1). The ATM protein is a serine-threonine kinase and a member of the PIKK (Phosphoinositide 3-Kinase-Like Kinase) family, which also includes DNA-PK (DNA Protein Kinase) and ATR (AT and Rad3-related protein). These proteins are associated with DNA damage surveillance, control of cell cycle checkpoints, and cell growth regulation. In response to DSBs. ATM in effect "raises the alarm" to DNA damage, phosphorylating many downstream effector targets such as p53, H2AX, Mdm-2, BRCA11, c-Ab1, Chk-2, 53BP1, and SMC-1 (Structural Maintenance of Chromosome-1).

This swift response acts to halt the cell cycle and stop DNA replication ATM; then facilitates DNA repair or triggers apoptosis based on the severity of the damage.

The MRN complex provides paradigm-shifting results of exceptional biomedical interest. MRN is among the earliest respondents to DSBs, and MRN mutations causes' human cancer predisposition diseases Nijmegen breakage syndrome and ATLD (Ataxia Telangiectasia-Like Disorder). MRNs 3-protein multidomain composition promotes its central architectural, structural, enzymatic, sensing, and signaling functions in DSB responses. To organize the MRN complex, the Mre11; exonuclease directly binds NBS1 (Nijmegen Breakage Syndrome 1) DNA, and Rad50. Rad50, which is a SMC related protein, employs it's ABC (ATP-Binding Cassette) ATPase, Zn hook, and coiled coils to bridge DSBs and facilitate DNA end processing by Mre11. Another mammalian protein that participates in the HDR process is the carboxy-terminal binding protein (CtBP)-interacting protein (CtIP). CtIP is known to function in 5' strand resection during homologous recombination independent of or in concert with the MRN complex. Recently EXD2 (also known as EXDL2) was characterized as an exonuclease essential for DSB resection and efficient HR. EXD2 is recruited to chromatin in a damage-dependent manner and confers resistance to DSB-inducing agents. EXD2 functionally interacts with the MRN complex to accelerate resection through its 3'-5' exonuclease activity, which efficiently processes double-stranded DNA substrates containing nicks (Broderick et al. Nat Cell Biol. 2016).

Subsequent steps of DSB repair through homologous recombination include DNA-end recognition, possibly by Rad52, and nucleolytic processing of the broken ends of DNA into 3-end single-stranded DNA. This single-stranded DNA is bound by the Rad51 protein which mediates crucial steps in the reaction, including the search for a homologous duplex template DNA and the formation of joint molecules between the broken DNA ends and the repair template. Rad51 is phosphorylated by c-Ab1 and this response contributes to the down-regulation of Rad51 activity in ATP-dependent DNA strand exchange reactions. Rad51 protein assembles with single-stranded DNA to form the helical nucleoprotein filament that promotes DNA strand exchange, a basic step of homologous recombination. Rad54 protein interacts with this Rad51 nucleoprotein filament and stimulates its DNA pairing activity, suggesting that Rad54 protein is a component of the nucleoprotein complex involved in the DNA homology search. The binding of Rad54 protein significantly stabilizes the Rad51 nucleoprotein filament formed on either single-stranded DNA or double-stranded DNA. The Rad54-stabilized nucleoprotein filament is more competent in DNA strand exchange and acts over a broader range of solution conditions. The co-assembly of an interacting partner with the Rad51; nucleoprotein filament represents a novel means of stabilizing the biochemical entity central to homologous recombination, and reveals a new function of Rad54 protein. The roles played by BRCA1 and BRCA2 in DSB repair by homologous recombination appear to be somewhat different. Despite the apparent dissimilarity in protein sequence and structure, both BRCA1 and BRCA2 have common biological functions. Their levels are highest during S phase, which is suggestive of functions during DNA replication. Both are localized to the nucleus in somatic cells, where they co-exist in characteristic sub-nuclear foci that redistribute following DNA damage. BRCA2 controls the intracellular transport and function of Rad51. In BRCA2– deficient cells, Rad51 (which does not contain a consensus nuclear localization signal) is inefficiently transported into the nucleus, which suggests that one function of BRCA2 is to move Rad51 from its site of synthesis to its site of activity. In addition, BRCA2 also appears to control the enzymatic activity of Rad51. Addition of peptides containing the Rad51-binding BRC repeat BRC3, BRC4 or BRC7 inhibits nucleoprotein filament formation. BRCA2 might not directly control Rad51 function, since the stoichiometry of their interaction is possibly low and does not appear to be greatly altered following DNA damage.

Once the homologous DNA has been identified, the subsequent step leads to Strand Invasion and D-loop formation. Damaged DNA strand invades the undamaged DNA duplex in a process referred to as DNA strand exchange. Upon joint-molecule formation and DNA synthesis, branched DNA structures called Holliday junctions can form as late intermediates in homologous recombination. Holliday junctions can slide, or branch-migrate, along the joined DNAs. Branch migration extends the heteroduplex DNA region between identical recombination partners and might thereby provide a mechanism to prevent recombination between repetitive sequences that are dispersed throughout the genome. A DNA Polymerase then extends the 3 end of the invading strand and subsequent ligation by DNA Ligase-I yields a hetero-duplexed DNA structure. Completion of recombination requires the Resolution of Holliday junctions, in order to separate the recombining partners. One well-characterized way of resolving Holliday junctions requires the enzymatic action of a Resolvase. This recombination intermediate is resolved and the precise, error-free correction of the DSB is complete.

DNA Nucleases

Any appropriate nuclease may be used to cleave a predetermined target site and subsequently initiate cellular repair pathways. In addition to the donor DNA template which contains at least one transcription factor binding site, a nuclease may be delivered to a cell to create a break at a target site and induce cellular DNA repair. The nuclease may comprise heterologous DNA-binding and cleavage domains (e.g., Cpf1, Cas9, zinc finger nucleases; TALENs, and meganuclease DNA-binding domains with heterologous cleavage domains) or, alternatively, the DNA-binding domain of a naturally-occurring nuclease may be altered to bind to a selected target site (e.g., a meganuclease that has been engineered to bind to site different than the cognate binding site). For example, engineering of homing endonucleases with tailored DNA-binding specificities has been described, see. Chames et al. (2005) Nucleic Acids Res 33(20):e178; Amould et al. (2006) J. Mol. Biol. 355:443-458 and Grizot et al (2009) Nucleic Acids Res July 7 e publication. In addition, engineering of ZFPs has also been described. See, e.g., U.S. Pat. Nos. 6,534,261; 6,607,882; 6,824,978; 6,979,539; 6,933,113; 7,163,824; and 7,013,219.

In certain embodiments, the nuclease comprises a meganuclease (homing endonuclease) domain. Naturally-occurring meganucleases recognize 15-40 base-pair cleavage sites and are commonly grouped into four families: the LAGLIDADG family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-PpoI, I-SceII, I-CreI, I-TeVI, I-TevII and I-TevIII. Their recognition sequences are known. See also U.S. Pat. Nos. 5,420,032; 6,833,252; Belfort et al. (1997) Nucleic Acids Res. 25:3379-3388; Dujon et al. (1989) Gene 82:115-118; Perler et al. (1994) Nucleic Acids Res. 22, 1125-1127;

Jasin (1996) Trends Genet. 12:224-228; Gimble et al. (1996) J. Mol. Biol. 263:163-180; Argast et al. (1998) J. Mol. Biol. 280:345-353 and the New England Biolabs catalogue. Thus, any meganuclease domain (or functional portion thereof) may be combined with any DNA-binding domain (e.g., ZFP, TALE) to form a nuclease.

In other embodiments, the nuclease is a zinc finger nuclease (ZFN). ZFNs comprise a zinc finger protein that has been engineered to bind to a target site in a gene of choice and cleavage domain or a cleavage half-domain.

Zinc finger binding domains can be engineered to bind to a sequence of choice. See, for example, Beerli et al. (2002) Nature Biotechnol. 20:135-141; Pabo et al. (2001) Ann. Rev. Biochem. 70:313-340; Isalan et a. (2001) Nature Biotechnol. 19:656-660; Segal et al., (2001) Curr. Opin. Biotechnol. 12:632-637; Choo et al. (2000) Curr. Opin. Struct. Biol. 10:411-416. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,453,242 and 6,534,261.

In still further embodiments, the nuclease comprises a compact TALEN (cTALEN). These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the TevI nuclease domain (see Beurdeley et al (2013) Nat Comm: 1-8 DOI: 10.1038/ncomms2782). Any TALENs may be used in combination with additional TALENs (e.g., one or more TALENs (cTALENs or FokI-TALENs) with one or more mega-TALs).

In certain embodiments, the nuclease comprises an RNA-guided DNA nuclease, e.g. derived from a CRISPR/Cas system. The CRISPR (clustered regularly interspaced short palindromic repeats) locus, which encodes RNA components of the system, and the cas (CRISPR-associated) locus, which encodes proteins (Jansen et al., 2002. Mol. Microbiol. 43: 1565-1575; Makarova et al., 2002. Nucleic Acids Res. 30: 482-496; Makarova et al., 2006, Biol. Direct 1: 7; Haft et al., 2005. PLoS Comput. Biol. 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally. Cas9 mediates cleavage of target DNA to create a double-stranded break within the protospacer.

Activity of the CRISPR/Cas system comprises of three steps: (i) insertion of alien DNA sequences into the CRISPR array to prevent future attacks, in a process called "adaptation", (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

The term guide RNA (gRNA) refers to an RNA molecule capable of forming a complex with a Cas protein e.g., Cas9 and wherein said complex is capable of targeting a DNA sequence i.e., genomic DNA sequence having a nucleotide sequence which is complementary to said gRNA.

The term "guide RNA" (gRNA) is a 20 bp RNA molecule that can form a complex with Cas9 and serve as the DNA recognition module.

The term "single guide RNA" (sgRNA), is a 20 bp RNA molecule that can form a complex with Cas9 and serve as the DNA recognition module. sgRNA is designed as a synthetic fusion of the CRISPR RNA (crRNA) and the trans-activating crRNA. With regard to Cas9, Cpf1 and other RNA-guided DNA nucleases, the term "RNA-guided DNA nuclease" encompasses both the nuclease alone or the nuclease bound to a gRNA or sgRNA.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

An exemplary RNA guided DNA nuclease of a Type II CRISPR System is a Cas9 protein or modified Cas9 or homolog of Cas9.

Cas9 may be altered to reduce, substantially reduce or eliminate nuclease activity.

According to one aspect, Cas9 nuclease activity is reduced, substantially reduced or eliminated by altering the RuvC nuclease domain or the HNH nuclease domain. According to one aspect, the RuvC nuclease domain is inactivated. According to one aspect, the HNH nuclease domain is inactivated. According to one aspect, the RuvC nuclease domain and the HNH nuclease domain are inactivated. According to an additional aspect, Cas9 proteins are provided where the RuvC nuclease domain and the HNH nuclease domain are inactivated. According to an additional aspect, nuclease-null Cas9 proteins are provided insofar as the RuvC nuclease domain and the HNH nuclease domain are inactivated. According to an additional aspect, a Cas9 nickase is provided where either the RuvC nuclease domain or the HNH nuclease domain is inactivated, thereby leaving the remaining nuclease domain active for nuclease activity. In this manner, only one strand of the double stranded DNA is cut or nicked.

According to an additional aspect, nuclease-null Cas9 proteins are provided where one or more amino acids in Cas9 are altered or otherwise removed to provide nuclease-null Cas9 proteins. According to one aspect, the amino acids include D10 and H840. According to an additional aspect, the amino acids include D839 and N863. According to one aspect, one or more or all of D10, H840, D839 and H863 are substituted with an amino acid which reduces, substantially eliminates or eliminates nuclease activity. According to one aspect, one or more or all of D10, H840, D839 and H863 are substituted with alanine. According to one aspect, a Cas9 protein having one or more or all of D10. H840, D839 and H863 substituted with an amino acid which reduces, substantially eliminates or eliminates nuclease activity, such as alanine, is referred to as a nuclease-null Cas9 or dCas9 and exhibits reduced or eliminated nuclease activity, or nuclease activity is absent or substantially absent within levels of detection. According to this aspect, nuclease activity for a dCas9 may be undetectable using known assays. i.e. below the level of detection of known assays.

According to one aspect, the Cas9 protein. Cas9 protein nickase or nuclease null Cas9 includes homologs and orthologs thereof which retain the ability of the protein to bind to the DNA and be guided by the RNA. According to one aspect, the Cas9 protein includes the sequence as set forth for naturally occurring Cas9 from *S. pyogenes* and protein sequences having at least 30%, 40%, 50%, 60%, 70%, 80%, 90%, 95%, 98% or 99% homology thereto and being a DNA binding protein, such as an RNA guided DNA binding protein. According to one aspect, an engineered Cas9-gRNA system is provided which enables RNA-guided genome regulation in cells by tethering transcriptional activation domains to either a nuclease-null Cas9 or to guide RNAs.

In some embodiments, the CAS protein is Cpf1, a putative class 2 CRISPR effector. Cpf1 mediates robust DNA interference with features distinct from Cas9. Cpf1 is a single RNA-guided endonuclease lacking tracrRNA, and it utilizes a T-rich protospacer-adjacent motif. Cpf1 cleaves DNA via a staggered DNA double-stranded break. two Cpf1 enzymes from Acidaminococcus and Lachnospiraceae have been shown to carry out efficient genome-editing activity in human cells. (Zetsche et al. Cell. 2015).

Target Sites

As described in detail above, DNA domains in the nucleases (ZFNs, TALENs and/or RNAs of CRISPR/Cas) can be engineered to bind to any sequence of choice m a locus. An engineered DNA-binding domain can have a novel binding specificity, compared to a naturally-occurring DNA-binding domain. Engineering methods include, but are not limited to, rational design and various types of selection. Rational design includes, for example, using databases comprising triplet (or quadruplet) nucleotide sequences and individual (e.g., zinc finger) amino acid sequences, in which each triplet or quadruplet nucleotide sequence is associated with one or more amino acid sequences of DNA binding domain which bind the particular triplet or quadruplet sequence.

In addition, a nuclease or a functional fragment thereof and a HDR protein or functional domain thereof may be linked together using any polypeptide linker, including for example, linkers of 5 amino acids or less, linkers of between 5 and 10 amino acids, linkers of between 10 and 20 amino acids, linkers of between 20 and 30 amino acids, linkers of between 10 and 100 amino acids, linkers of between 50 and 200 amino acids, linkers of between 100 and 300 amino acids, linkers of more than 300 amino acids.

Additionally, single guide RNAs can be engineered to bind to a target of choice in a genome by commonly known methods known in the art for creating specific RNA sequences. These single guide RNAs are designed to guide the Cas9 to any chosen target site.

Donors

Insertion of an exogenous sequence (also called a "donor sequence," "donor template" or "donor"), for example, for correction of a mutant gene or for increased expression of a wild-type gene can also be carried out. It will be readily apparent that the donor sequence is typically not identical to the genomic sequence where it is placed. A donor sequence can contain a non-homologous sequence flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

The donor polynucleotide can be DNA or RNA, single-stranded and/or double-stranded and can be introduced into a cell in linear or circular form. See. e.g., U.S. Patent Publication Nos. 20100047805; 20110281361; and 20110207221. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) Proc. Natl. Acad. Sci. USA 84:4959-4963; Nehls et al. (1996) Science 272: 886-889. Additional methods for protecting exogenous poly-nucleotides from degradation include, but are not limited to, addition of terminal amino group(s) and the use of modified internucleotide linkages such as, for example, phosphoro-thioates, phosphoramidates, and O-methyl ribose or deoxy-ribose residues.

A donor sequence may also be an oligonucleotide and be used for gene correction or targeted alteration of an endog-enous sequence. The oligonucleotide may be introduced to the cell on a vector, may be electroporated into the cell, or may be introduced via other methods known in the art. The oligonucleotide can be used to 'correct' a mutated sequence in an endogenous gene (e.g, the sickle mutation in beta globin), or may be used to insert sequences with a desired purpose into an endogenous locus.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid com-plexed with an agent such as a liposome or poloxamer, or can be delivered by viruses (e.g., adenovirus, AAV, herpes-virus, retrovirus, lentivirus and integrase defective lentivirus (IDLV)).

The donor is generally inserted so that its expression is driven by the endogenous promoter at the integration site, namely the promoter that drives expression of the endog-enous gene into which the donor is inserted. However, it will be apparent that the donor may comprise a promoter and/or enhancer, for example a constitutive promoter or an induc-ible or tissue specific promoter.

The donor molecule may be inserted into an endogenous gene such that all, some or none of the endogenous gene is expressed. For example, a transgene as described herein may be inserted into an endogenous locus such that some (N-ter-minal and/or C-terminal to the transgene) or none of the endogenous sequences are expressed, for example as a fusion with the transgene. In other embodiments, the trans-gene (e.g., with or without additional coding sequences such as for the endogenous gene) is integrated into any endog-enous locus, for example a safe-harbor locus, for example a CCR5 gene, a CXCR4 gene, a PPP1R12c (also known as AAVS1) gene, an albumin gene or a Rosa gene. See, e.g., U.S. Pat. Nos. 7,951,925 and 8,110,379; U.S. Publication Nos. 20080159996; 201000218264; 20100291048; 20120017290; 20110265198; 20130137104; 20130122591; 20130177983, and 20130177960 and U.S. Provisional Application No. 61/823,689).

When endogenous sequences (endogenous or part of the transgene) are expressed with the transgene, the endogenous sequences may be full-length sequences (wild-type or mutant) or partial sequences. Preferably the endogenous sequences are functional. Non-limiting examples of the function of these full length or partial sequences include increasing the serum half-life of the polypeptide expressed by the transgene (e.g., therapeutic gene) and/or acting as a carrier.

Furthermore, although not required for expression, exog-enous sequences may also include transcriptional or trans-lational regulatory sequences, for example, promoters, enhancers, insulators, internal ribosome entry sites, sequences encoding 2A peptides and/or polyadenylation signals.

In certain embodiments, the donor molecule comprises a sequence selected from the group consisting of a gene encoding a protein (e.g., a coding sequence encoding a protein that is lacking in the cell or in the individual or an alternate version of a gene encoding a protein), a regulatory sequence and/or a sequence that encodes a structural nucleic acid such as a microRNA or siRNA.

Delivery

The proteins and/or polynucleotides encoding the same and donor polynucleotides as described herein may be delivered to a target cell by any suitable means.

Methods of delivering proteins comprising nucleases as described herein are described, for example, in U.S. Pat. Nos. 6,453,242; 6,503,717; 6,534,261; 6,599,692; 6,607, 882; 6,689,558; 6,824,978; 6,933,113; 6,979,539; 7,013, 219; and 7,163,824.

Zinc finger, TALE or CRISPR/Cas proteins as described herein may also be delivered using vectors containing sequences encoding one or more of the zinc finger proteins, zinc finger nucleases, TAL-effector domain proteins, TAL-ENs and/or CRISPR/Cas protein(s). Donor encoding poly-nucleotides may be similarly delivered. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 8,586,526; 6,534,261; 6,607,882; 6,824,978; 6,933,113; 6,979,539; 7,013,219; and 7,163,824. Furthermore, it will be apparent that any of these vectors may comprise one or more zinc finger protein-encoding sequences, one or more CRISPR/ Cas-encoding sequences or one or more TALE-encoding sequences. Thus, when one or more nucleases or nuclease systems and/or donors are introduced into the cell, the nucleases or nuclease systems and/or donors may be carried on the same vector or on different vectors. When multiple vectors are used, each vector may comprise a sequence encoding one or multiple ZFPs, TALEs, nuclease comprising ZFPs and/or TALEs, CRISPR/Cas system and/or donors.

Conventional viral and non-viral based gene transfer methods can be used to introduce nucleic acids and/or donors in cells (e.g., mammalian cells) and target tissues. Such methods can also be used to administer nucleic acids and/or donors to cells in vitro. In certain embodiments, nucleic acids and donors are administered for in vivo or ex vivo gene therapy uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, Science 256:808-813 (1992); Nabel & Feigner, TIBTECH 11:211-217 (1993), Mitani & Caskey, TIBTECH 11:162-166 (1993); Dillon, TIBTECH 11:167-175 (1993); Miller, Nature 357:455-460 (1992); Van Brunt, Biotechnology 6(10):1149-1154 (1988), Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Bohm (eds.) (1995); and Yu et al., Gene Therapy 1:13-26 (1994).

Methods of non-viral delivery of nucleic acids include electroporation, lipofection, microinjection, biolistics, virosomes, liposomes, immunoliposomes, polycation or lipid: nucleic acid conjugates, naked DNA, mRNA, artificial virions, and agent-enhanced uptake of DNA or can be delivered to plant cells by bacteria or viruses (e.g., *Agrobacterium, Rhizobium* sp. NGR234, Sinorhizoboiummeliloti, *Mesorhizobium loti*, tobacco mosaic virus, potato virus X, cauliflower mosaic virus and cassaya vein mosaic virus. See, e.g., Chung et al. (2006) Trends Plant Sci. 11(1):1-4. Sonoporation using. e.g., the Sonitron 2000 system (Rich-Mar) can also be used for delivery of nucleic acids. In one embodiment, one or more nucleic acids are delivered as mRNA. Also optional is the use of capped or modified mRNAs to increase translational efficiency and/or mRNA stability.

Additional exemplary nucleic acid delivery systems include those provided by Amaxa® Biosystems (Cologne, Germany), Maxcyte, Inc. (Rockville, Md.), BTX Molecular Delivery Systems (Holliston, Mass.) and Copernicus Therapeutics Inc., (see for example U.S. Pat. No. 6,008,336). Lipofection is described in e.g., U.S. Pat. Nos. 5,049,386, 4,946,787; and 4,897,355) and lipofection reagents are sold commercially (e.g., Transfectam™, Lipofectin™ and Lipofectamine™ RNAiMAX). Cationic and neutral lipids that are suitable for efficient receptor-recognition lipofection of polynucleotides include those of Feigner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485, 054, 4,501,728, 4,774.085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiamid et al (2009) Nature Biotechnology 27(7) p. 643).

The use of RNA or DNA viral based systems for the delivery of nucleic acids and/or donors take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of proteins include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV). Simian Immunodeficiency virus (SIV), human immunodeficiency virus (HIV), and combinations thereof (see, e.g. Buchscher et al., J. Virol. 66:2731-2739 (1992); Johann et al., J. Virol. 66:1635-1640 (1992); Sommerfelt et al., Virol. 176:58-59 (1990); Wilson et al, J. Virol. 63:2374-2378 (1989); Miller et al., J. Virol. 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors is described in a number of publications, including U.S. Pat. No. 5,173,414; Tratschin et al., Mol. Cell. Biol. 5:3251-3260 (1985); Tratschin et al., Mol. Cell. Biol. 4:2072-2081 (1984); Hermonat & Muzyczka, PNAS 81:6466-6470 (1984); and Samulski et al., J. Virol. 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., Blood 85:3048-305 (1995); Kohn et al., Nat. Med. 1:1017-102 (1995); Malech et al., PNAS 94:22 12133-12138 (1997)). PA317/pLASN was the first therapeutic vector used in a gene therapy trial. (Blaese et al., Science 270:475-480 (1995)). Transduction efficiencies of 50% or greater have been observed for MFG-S packaged vectors. (Ellem et al., Immunol Immunother. 44(1):10-20 (1997); Dranoff et al., Hum. Gene Ther. 1:111-2 (1997).

Recombinant adeno-associated virus vectors (rAAV) are a promising alternative gene delivery systems based on the defective and nonpathogenic parvovirus adeno-associated type virus. The vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., Lancet 351:9117 1702-3 (1998). Kearns et al., Gene Ther. 9:748-55 (1996)). Other AAV serotypes, including AAV 1, AAV3, AAV4, AAV5, AAV6 and AAV8, AAV 8.2, AAV9, and AAV rh10 and pseudotyped AAV such as AAV2/8, AAV2/5 and AAV2/6 can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vin, including nondividing, differentiated cells such as those found in liver, kidney and muscle.

Conventional Ad vectors have a large carrying capacity. An example of the use of an Ad vector in a clinical trial involved polynucleotide therapy for antitumor immunization with intramuscular injection (Sternan et al., Hum. Gene Ther. 7:1083-9 (1998)). Additional examples of the use of adenovirus vectors for gene transfer in clinical trials include Rosenecker et al., Infection 24:1 5-10 (1996); Sterman et al., Hum. Gene Ther. 9:7 1083-1089 (1998); Welsh et al., Hum. Gene Ther. 2:205-18 (1995); Alvarez et al., Hum. Gene Ther. 5:597-613 (1997); Topf et al., Gene Ther. 5:507-513 (1998); Sterman et al., Hum. Gene Ther. 7:1083-1089 (1998).

Packaging cells are used to form virus particles that are capable of infecting a host cell. Such cells include 293 cells, which package adenovirus, AAV, and .psi.2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example AAV vectors used in gene therapy typically only possess inverted terminal repeat (ITR)

sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additionally, AAV can be produced at clinical scale using baculovirus systems (see U.S. Pat. No. 7,479,554).

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., Proc. Natl. Acad. Sci. USA 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

In some embodiments, one or more polynucleotide of the present invention may be combined on the same construct. In some embodiments, one or more polynucleotide of the present invention may be on different constructs. In Some embodiments, one or more polynucleotide of the present invention may be packed in different viruses or vectors, and any polynucleotide may have a separate promotor controlling transcription of said polynucleotide. In some embodiments, one or more polynucleotide of the present invention may be expressed under the same promotor.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a ZFP nucleic acid (gene or cDNA), and re-infused back into the subject organism (e.g., patient). Various cell types suitable for ex vivo transfection are well known to those of skill in the art (see, e.g., Freshney et al., Culture of Animal Cells, A Manual of Basic Technique (3rd ed. 1994)) and the references cited therein for a discussion of how to isolate and culture cells from patients).

Suitable cells include but not limited to eukaryotic and prokaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NSO, SP2/0-Ag14, HeLa, HEK293 (e.g., HEK293-F, HEK293-H, HEK293-T), and perC6 cells, any plant cell (differentiated or undifferentiated) as well as insect cells such as Spodopterafugiperda (Sf), or fungal cells such as *Saccharomyces. Pichia* and *Schizosaccharomyces*. In certain embodiments, the cell line is a CHO-K1, MDCK or HEK293 cell line. Additionally, primary cells may be isolated and used ex vivo for reintroduction into the subject to be treated following treatment with the nucleases (e.g. ZFNs or TALENs) or nuclease systems (e.g. CRISPR/Cas). Suitable primary cells include peripheral blood mononuclear cells (PBMC), and other blood cell subsets such as, but not limited to, CD4+ T cells or CD8+ T cells. Suitable cells also include stem cells such as, by way of example, embryonic stem cells, induced pluripotent stem cells, hematopoietic stem cells (CD34+), neuronal stem cells and mesenchymal stem cells.

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF. IFN-.gamma. and TNF-alpha are known (as a non-limiting example see. Inaba et al., J. Exp. Med. 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+(T cells), CD45+(panB cells), GR-1 (granulocytes), and Iad (differentiated antigen presenting cells) (as a non-limiting example see Inaba et al., J. Exp. Med. 176: 1693-1702 (1992)).

Stem cells that have been modified may also be used in some embodiments. For example, stem cells that have been made resistant to apoptosis may be used as therapeutic compositions where the stem cells also contain the ZFPs, TALEs, ZFNs, TALENS, CRISPR/Cas systems and/or donors of the invention. Resistance to apoptosis may come about, for example, by knocking out BAX and/or BAK using BAX- or BAK-specific nucleases (see, U.S. Patent Publication No. 2010/0003756) in the stem cells, or those that are disrupted in a caspase, again using caspase-6 specific ZFNs for example. Alternatively, resistance to apoptosis can also be achieved by the use of caspase inhibitors like Z-VAD-FMK (carbobenzoxy-valyl-alanyl-aspartyl-JO-methyll-fluoromethylketone).

Vectors (e.g., retroviruses, adenoviruses, liposomes, etc.) containing therapeutic compositions as described herein can also be administered directly to an organism for transduction of cells in vivo. Alternatively, naked DNA or mRNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are disclosed, for example, in U.S. Pat. No. 5,928,638. Vectors useful for introduction of transgenes into hematopoietic stem cells, e.g., CD34.sup.+ cells, include adenovirus Type 35.

Vectors suitable for introduction of transgenes into immune cells (e.g., T-cells) include non-integrating lentivirus vectors. See, for example, U.S. Patent Publication No 20090117617.

Pharmaceutically acceptable carriers are determined in part by the particular composition being administered, as well as by the particular method used to administer the composition.

Accordingly, there is a wide variety of suitable formulations of pharmaceutical compositions available, as described below (see, e.g., Remington's Pharmaceutical Sciences, 17th ed., 1989).

Applications

The disclosed compositions may be used in methods for genome editing and increasing the rate of homology directed recombination at target site in the genome of a cell. Such methods utilizing the compositions increase the rate of DNA insertion by homologous directed recombination at a target site by at least 10%, more preferably at least 50%, more preferably at least 10M/o compared to a donor molecule which does not contain a transcription factor binding site. Such methods also reduce the rate of off-target excision by at least 10%, more preferably at least 50%, more preferably at least 100% compared to a donor molecule which does not contain a transcription factor binding site. Thus, the disclosed compositions and methods can be used for any application in which it is desired to increase nuclease-mediated genomic modification in any cell type, including clinical applications nuclease-based therapies feasible in a clinical setting as well as agricultural (plant) applications. For example, the methods described herein will improve the therapeutic effect of ZFNs, TALENs, and/or CRISPR/Cas systems in the following scenarios: ex vivo and in vivo gene disruption (CCR5) in CD34+ cells (see, e.g., U.S. Pat. No. 7,951,925); ex vivo and in vivo gene correction of hemoglobinopathies in CD34+ cells (see, e.g., U.S. Application No. 61/694,693); and/or ex vivo and in vivo gene addition to albumin locus for therapy of lysosomal storage diseases and hemophilias (see, e.g., U S. Patent Publication Nos. 20140017212 and 20130177983). The disclosed compositions and methods may also be used in the manufacture of a medicament or pharmaceutical composition for treating genetic diseases in a patient.

In addition, the methods and compositions described herein can be used to generate model organisms and cell lines, including the generation of stable knock-out cells in any given organism. While ZFN, TALENs and CRISPR/Cas systems offer the ability to knock-out any given gene in cell lines or model organism, in the absence of selection marker these events however can be very rare. Accordingly, the methods described herein, which significantly increase the rate of targeted gene correction, can be used to generate cell lines with new properties. This includes cell lines used for the production of biologicals like Hamster (CHO) cell lines or cell lines for the production of several AAV serotypes like human HEK 293 cells or insect cells like Sf9 or Sf21 or genomically-modified plants and plant lines.

The methods and compositions of the invention can also be used in the production of non-human transgenic organisms. Transgenic animals can include those developed for disease models, as well as animals with desirable traits. Embryos may be treated using the methods and compositions of the invention to develop transgenic animals. In some embodiments, suitable embryos may include embryos from small mammals (e.g., rodents, rabbits, etc.), companion animals, livestock, and primates. Non-limiting examples of rodents may include mice, rats, hamsters, gerbils, and guinea pigs. Non-limiting examples of companion animals may include cats, dogs, rabbits, hedgehogs, and ferrets. Non-limiting examples of livestock may include horses, goats, sheep, swine, llamas, alpacas, and cattle. Non-limiting examples of primates may include capuchin monkeys, chimpanzees, lemurs, macaques, marmosets, tamarins, spider monkeys, squirrel monkeys, and vervet monkeys. In other embodiments, suitable embryos may include embryos from fish, reptiles, amphibians, or birds. Alternatively, suitable embryos may be insect embryos, for instance, a *Drosophila* embryo or a mosquito embryo.

Transgenic organisms contemplated by the methods and compositions of this invention also include transgenic plants and seeds. Examples of suitable transgenes for introduction include exogenous nucleic acid sequence that may comprise a sequence encoding one or more functional polypeptides (e.g., a cDNA), with or without one or more promoters and/or may produce one or more RNA sequences (e.g., via one or more shRNA expression cassettes), which impart desirable traits to the organism. Such traits in plants include, but are not limited to, herbicide resistance or tolerance; insect resistance or tolerance; disease resistance or tolerance (viral, bacterial, fungal, nematode); stress tolerance and/or resistance, as exemplified by resistance or tolerance to drought, heat, chilling, freezing, excessive moisture, salt stress; oxidative stress; increased yields; food content and makeup; physical appearance; male sterility; drydown; standability; prolificacy; starch quantity and quality; oil quantity and quality; protein quality and quantity; amino acid composition; and the like. Of course, any two or more exogenous nucleic acids of any description, such as those conferring herbicide, insect, disease (viral, bacterial, fungal, nematode) or drought resistance, male sterility, drydown, standability, prolificacy, starch properties, oil quantity and quality, or those increasing yield or nutritional quality may be employed as desired. In certain embodiments, the exogenous nucleic acid sequence comprises a sequence encoding a herbicide resistance protein (e.g., the AAD (aryloxyalkanoatedioxygenase) gene) and/or functional fragments thereof.

Kits

In another aspect, the invention provides kits that are useful for increasing gene disruption and/or targeted integration following nuclease-mediated cleavage of a cell's genome. The kits typically include a composition including one or more nucleases that bind to a target site, a donor DNA template and a transcription factor capable of binding the donor DNA template, as well as instructions for introducing the composition into the cells such that nuclease-mediated gene disruption and/or targeted integration is enhanced.

Optionally, cells containing the target site(s) of the nuclease may also be included in the kits described herein.

In certain embodiments, the kits comprise at least one construct with the target gene and a known nuclease capable of cleaving within the target gene. Such kits are useful for optimization of cleavage conditions in a variety of varying host cell types.

Other kits contemplated by the invention may include a nuclease capable of cleaving within a known target locus within a genome, a donor DNA template capable of being bound by at least one transcription factor and the at least one transcription factor. The kit may include the DNA donor and transcription factor separately or already bound.

The kits typically contain polynucleotides encoding one or more nucleases and donor polynucleotides as described herein as well as instructions for introducing the nucleases and/or donor polynucleotide to cells. The kits can also contain cells, buffers for transformation of cells, culture media for cells, and/or buffers for performing assays.

Typically, the kits also contain a label which includes any material such as instructions, packaging or advertising leaflet that is attached to or otherwise accompanies the other components of the kit.

REFERENCES

1. Ahmad et al., (1992) Cancer Res. 52:4817-4820
2. Alvarez et al., (1997) Hum. Gene Ther. 5:597-613
3. Anderson, (1992) Science 256:808-813
4. Argast et al. (1998) J Mol. Biol. 280:345-353
5. Amould et al. (2006) J. Mol. Biol. 355:443-458
6. Beerli et al. (2002) Nature Biotechnol. 20:135-141
7. Behr et al., (1994) Bioconjugate Chem. 5:382-389
8. Belfort et al. (1997) Nucleic Acids Res. 25:3379-3388
9. Beurdeley et al (2013) Nat Comm: 1-8 DOI: 10.1038/ncomms2782
10. Blaese et al., (1995) Cancer Gene Ther. 2:291-297
11 Blaese et al., (1995) Science 270:475-480
12. Broderick et al. (2016) Nat Cell Biol.
13. Buchscher et al., (1992) J. Virol. 66:2731-2739
14. Chames et al. (2005) Nucleic Acids Res 33(20):e178
15. Chang et al. (1987) Proc. Natl. Acad. Sci. USA 84:4959-4963
16. Choo et al. (2000) Curr. Opin. Struct. Biol. 10:411-416
17. Chung et al. (2006) Trends Plant Sci. 11(1):1-4
18. Crystal, (1995) Science 270:404-410
19. Dillon, (1993) TIBTECH 11:167-175
20. Dranoff et al., (1997) Hum. Gene Ther. 1:111-2
21. Dujon et al. (1989) Gene 82:115-118
22. Dunbar et al., (1995) Blood 85:3048-305
23. Ellem et al., (1997) Immunol Immunother. 44(1):10-20
24. Fields et al. (1989) Nature 340:245-246
25. Freshney et al., (1994) Culture of Animal Cells, A Manual of Basic Technique (3rd ed.)
26. Gao et al., (1995) Gene Therapy 2:710-722
27. Gimble et al. (1996) J. Mol. Biol. 263:163-180
28. Grizot et al (2009) Nucleic Acids Res July 7 e publication
29. Haddada et al., (1995) Current Topics in Microbiology and Immunology Doerfler and Bohm (eds.)
30. Haft et al., (2005) PLoS Comput. Biol. 1: e60
31. Han et al., (1995) Proc. Natl. Acad. Sci. USA 92:9747-9751
32. Hermonat & Muzyczka, (1984) PNAS 81:6466-6470
33. Inaba et al., (1992) J. Exp. Med. 176:1693-1702
34. Isalan et al. (2001) Nature Biotechnol. 19-656-660
35. Jansen et al., (2002) Mol. Microbiol. 43: 1565-1575
36. Jasin (1996) Trends Genet. 12:224-228
37. Johann et al., (1992) J. Virol. 66:1635-1640
38. Kearns et al., (1996) Gene Ther. 9:748-55
39. Kohn et al., (1995) Nat. Med. 1:1017-102
40. Kotin, (1994) Human Gene Therapy 5:793-801
41. Kremer & Perricaudet, (1995) British Medical Bulletin 51(1):31-44

42. MacDiamid et al (2009) Nature Biotechnology 27(7) p. 643
43. Makarova et al., (2002). Nucleic Acids Res. 30: 482-496
44. Makarova et al., (2006). Biol. Direct 1: 7
45. Malech et al., (1997) PNAS 94:22 12133-12138
46. Miller et al., (1991) J. Virol. 65:2220-2224
47. Miller. (1992) Nature 357:455-460
48. Mitani & Caskey, (1993) TIBTECH 11:162-166
49. Muzyczka, (1994) J. Clin. Invest. 94:1351
50. Nabel & Felgner, (1993) TIBTECH 11:211-217
51. Nehls et al. (1996) Science 272:886-889
52. New England Biolabs Catalogue, Beverly, Mass.
53. Pabo et al. (2001) Ann. Rev. Biochem. 70:313-340
54. Perler et al. (1994) Nucleic Acids Res. 22, 1125-1127
55. Remington's Pharmaceutical Sciences, (1989) 17th ed.
56. Remy et al., (1994) Bioconjugate Chem. 5:647-654
57. Rosenecker et al., (1996) Infection 24:1 5-10
58. Samulski et al. (1989) J. Virol. 63:03822-3828
59. Segal et al. (2001) Curr. Opin. Biotechnol. 12:632-637
60. Sommerfelt et al., (1990) Virol. 176:58-59
61. Sterman et al., (1998) Hum. Gene Ther. 9:7 1083-1089
62. Topf et al., (1998) Gene Ther. 5:507-513
63. Tratschin et al., (1984) Mol. Cell. Biol. 4:2072-2081
64. Tratschin et al., (1985) Mol. Cell. Biol. 5:3251-3260
65 Van Brunt, (1988) Biotechnology 6(10): 1149-1154
66. Vigne, (1995) Restorative Neurology and Neuroscience 8:35-36
67. Wagner et al., (1998) Lancet 351:9117 1702-3
68. Welsh et al., (1995) Hum. Gene Ther. 2:205-18
69. West et al., (1987) Virology 160.38-47
70. Wilson et al., (1989) J. Virol. 63:2374-2378
71. Yu et al., (1994) Gene Therapy 1:13-26
72. Zetsche et al. (2015) Cell. 163(3):759-71
73. U.S. Pat. No. 4,186,183
74. U.S. Pat. No. 4,217,344
75. U.S. Pat. No. 4,235,871
76. U.S. Pat. No. 4,261,975
77. U.S. Pat. No. 4,485,054
78. U.S. Pat. No. 4,501,728
79. U.S. Pat. No. 4,774,085
80. U.S. Pat. No. 4,797,368
81. U.S. Pat. No. 4,837,028
82. U.S. Pat. No. 4,897,355
83. U.S. Pat. No. 4,946,787
84. U.S. Pat. No. 5,049,386
85. U.S. Pat. No. 5,173,414
86. U.S. Pat. No. 5,176,996
87. U.S. Pat. No. 5,420,032
88. U.S. Pat. No. 5,422,251
89. U.S. Pat. No. 5,585,245
90. U.S. Pat. No. 5,928,638
91. U.S. Pat. No. 6,453,242
92. U.S. Pat. No. 6,503,717
93. U.S. Pat. No. 6,534,261
94. U.S. Pat. No. 6,599,692
95. U.S. Pat. No. 6,607,882
96. U.S. Pat. No. 6,689,558
97. U.S. Pat. No. 6,824,978
98. U.S. Pat. No. 6,833,252
99. U.S. Pat. No. 6,933,113
100. U.S. Pat. No. 6,979,539
101. U.S. Pat. No. 7,013,219
102. U.S. Pat. No. 7,163,824
103. U.S. Pat. No. 7,479,554
104. U.S. Pat. No. 7,951,925
105. U.S. Pat. No. 8,110,379
106. U.S. Pat. No. 8,586,526

107. U.S. Patent Publication No. 2007/0117128
108. U.S. Patent Publication No. 2008/0159996
109. U.S. Patent Publication No. 2009/0117617
110. U.S. Patent Publication No. 2010/0218264
111. U.S. Patent Publication No. 2010/0291048
112. U.S. Patent Publication No. 2010/0003756
113. U.S. Patent Publication No. 2010/0047805
114. U.S. Patent Publication No. 2011/0207221
115. U.S. Patent Publication No. 2011/0265198
116. U.S. Patent Publication No. 2011/0281361
117. U.S. Patent Publication No. 2012/0017290
118. U.S. Patent Publication No. 2013/0122591
119. U.S. Patent Publication No. 2013/0137104
120. U.S. Patent Publication No. 2013/0177960
121. U.S. Patent Publication No. 2013/0177983
122. U.S. Patent Publication No. 2014/0017212
123. U.S. Provisional Application No. 61/823,689
124. U.S. Provisional Application No. 61/694,693
125. PCT International Publication No. WO/1991/016024
126. PCT International Publication No. WO/1991/017424
127 PCT International Publication No. WO/1993/024641
128. PCT International Publication No. WO/1998/044350
129. PCT International Application No. PCT/US94/05700

What is claimed is:

1. A composition comprising a donor DNA template molecule comprising a single stranded DNA (ssDNA) donor portion and a double stranded DNA (dsDNA) portion, wherein the dsDNA portion comprises at least one transcription factor binding site, wherein the transcription factor binding site is a binding site for a transcription factor selected from the group consisting of Sp1, TBP, TAFs, E2F, E-box and YY1; and wherein the ssDNA donor portion comprises a) a non-homologous sequence flanked by b) two regions homologous to a target gene.

2. The composition of claim 1, further comprising (A) an RNA-guided DNA nuclease, or a polynucleotide encoding an RNA-guided DNA nuclease; or (B) a guide RNA, or a polynucleotide encoding a guide RNA; or (C) an RNA-guided DNA nuclease, or a polynucleotide encoding an RNA-guided DNA nuclease, and a guide RNA, or a polynucleotide encoding a guide RNA.

3. The composition of claim 2, wherein the RNA-guided DNA nuclease is a *S. pyogenes* Cas9 nuclease.

4. The composition of claim 1, wherein the composition further comprises an inhibitor of non-homologous end joining.

5. The composition of claim 1, wherein the composition further comprises a proliferation factor.

6. The composition of claim 1, wherein the composition comprises an Sp1 transcription factor.

7. The composition of claim 1, wherein the donor DNA template molecule further comprises a second double stranded DNA (dsDNA) portion, wherein the second dsDNA portion comprises a second transcription factor binding site.

8. The composition of claim 7, wherein the second transcription factor binding site binds a different transcription factor than the first transcription factor binding site.

9. A pharmaceutical composition comprising the composition of claim 1.

10. A method for editing a genome in a cell comprising delivering to the cell a donor DNA template molecule comprising a single stranded DNA (ssDNA) donor portion and a double stranded DNA (dsDNA) portion, wherein the dsDNA portion comprises at least one transcription factor binding site, wherein the transcription factor binding site is a binding site for a transcription factor selected from the group consisting of Sp1, TBP, TAFs, E2F, E-box and YY1, and wherein the ssDNA donor portion comprises a) a non-homologous sequence flanked by b) two regions homologous to a target gene.

11. The method of claim 10, further comprising delivering to the cell (A) an RNA-guided DNA nuclease, or a polynucleotide encoding an RNA-guided DNA nuclease; or (B) a guide RNA, or a polynucleotide encoding a guide RNA; or (C) an RNA-guided DNA nuclease, or a polynucleotide encoding an RNA-guided DNA nuclease, and a guide RNA, or a polynucleotide encoding a guide RNA.

\*    \*    \*    \*    \*